United States Patent [19]
Alexander

[11] Patent Number: 5,217,467
[45] Date of Patent: Jun. 8, 1993

[54] DEVICE FOR ASSISTING CHILDBIRTH

[75] Inventor: Gary E. Alexander, Baton Rouge, La.

[73] Assignee: Medisys Technologies, Inc., Baton Rouge, La.

[21] Appl. No.: 982,016

[22] Filed: Nov. 24, 1992

Related U.S. Application Data

[63] Continuation of Ser. No. 851,068, Mar. 13, 1992, abandoned, which is a continuation-in-part of Ser. No. 522,592, May 14, 1990, Pat. No. 5,122,148.

[51] Int. Cl.$^5$ .................. A61B 17/00; A61B 19/00
[52] U.S. Cl. .................................. 606/122; 606/121; 606/119
[58] Field of Search .................. 606/119-126

[56] References Cited

U.S. PATENT DOCUMENTS

| | | |
|---|---|---|
| 713,166 | 11/1902 | St. Cyr . |
| 1,690,942 | 11/1928 | Odell . |
| 1,782,814 | 11/1930 | Froehlic . |
| 3,139,886 | 7/1964 | Tallman et al. . |
| 3,550,595 | 12/1970 | Laufe . |
| 3,605,748 | 9/1971 | Salinas-Benavides . |
| 3,665,925 | 5/1972 | Dersookian . |
| 3,785,381 | 1/1974 | Lower et al. . |
| 3,789,849 | 2/1974 | Laufe et al. . |
| 4,875,482 | 10/1989 | Hariri et al. . |
| 4,997,391 | 7/1986 | Janko . |

FOREIGN PATENT DOCUMENTS

| | | | |
|---|---|---|---|
| 2233840 | 1/1974 | Fed. Rep. of Germany | 606/121 |
| 2925386 | 1/1981 | Fed. Rep. of Germany | 606/122 |
| WO8911253 | 11/1989 | France . | |
| 8911253 | 11/1989 | World Int. Prop. O. | 606/122 |

Primary Examiner—Stephen C. Pellegrino
Assistant Examiner—Glenn K. Dawson
Attorney, Agent, or Firm—William David Kiesel; Robert C. Tucker; C. Dean Domingue

[57] ABSTRACT

A device to assist in removing a fetus from a woman's birth canal during childbirth is provided having a pliable, elongated, hollow member sized to fit over the head of the fetus, collar means attached at one end of the member to restrict the opening of the hollow member at that end to the desired size and insertion means for inserting the elongated, hollow member over the head of the fetus. The hollow member can be linearly reinforced along it's length.

13 Claims, 10 Drawing Sheets

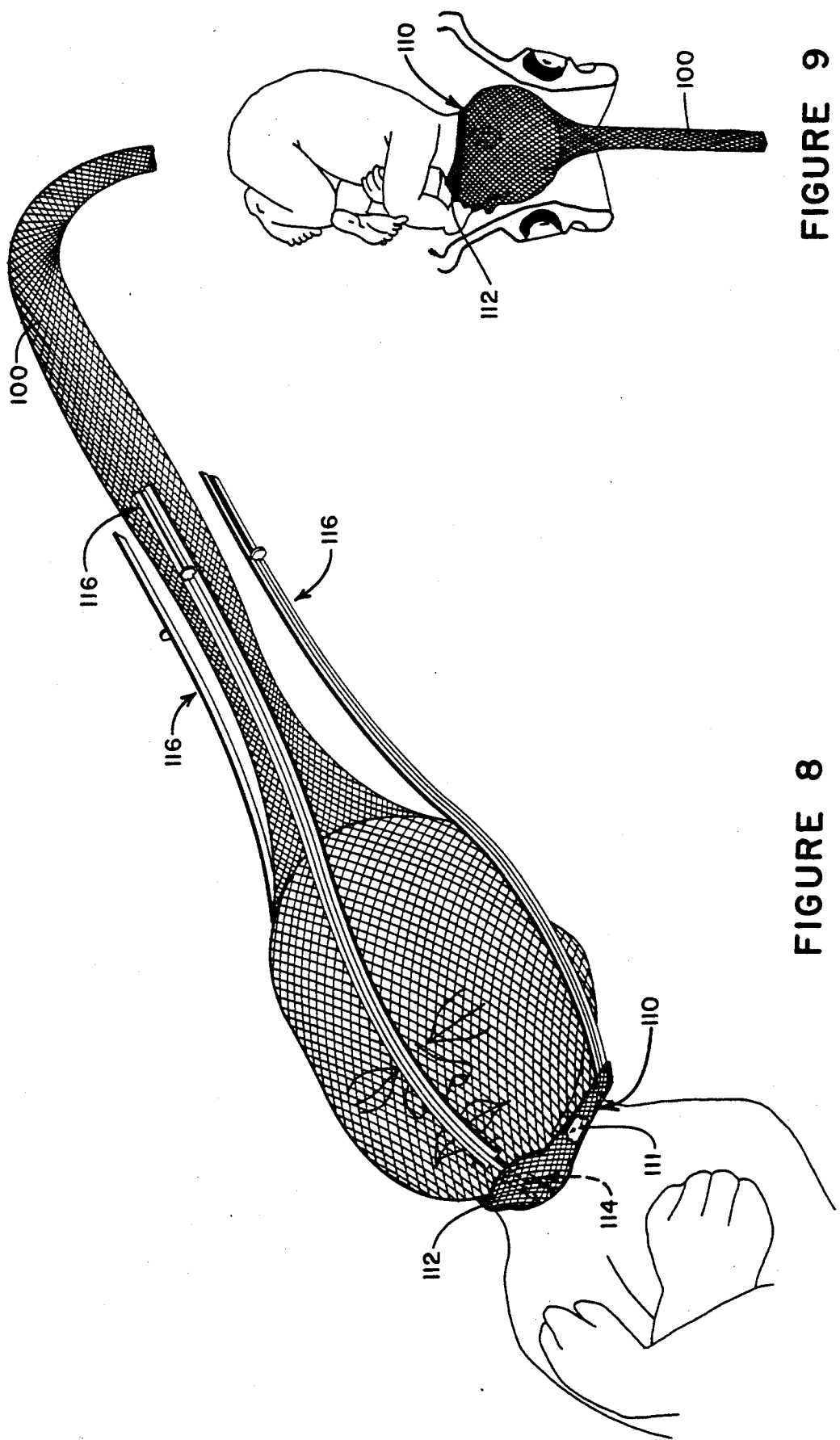

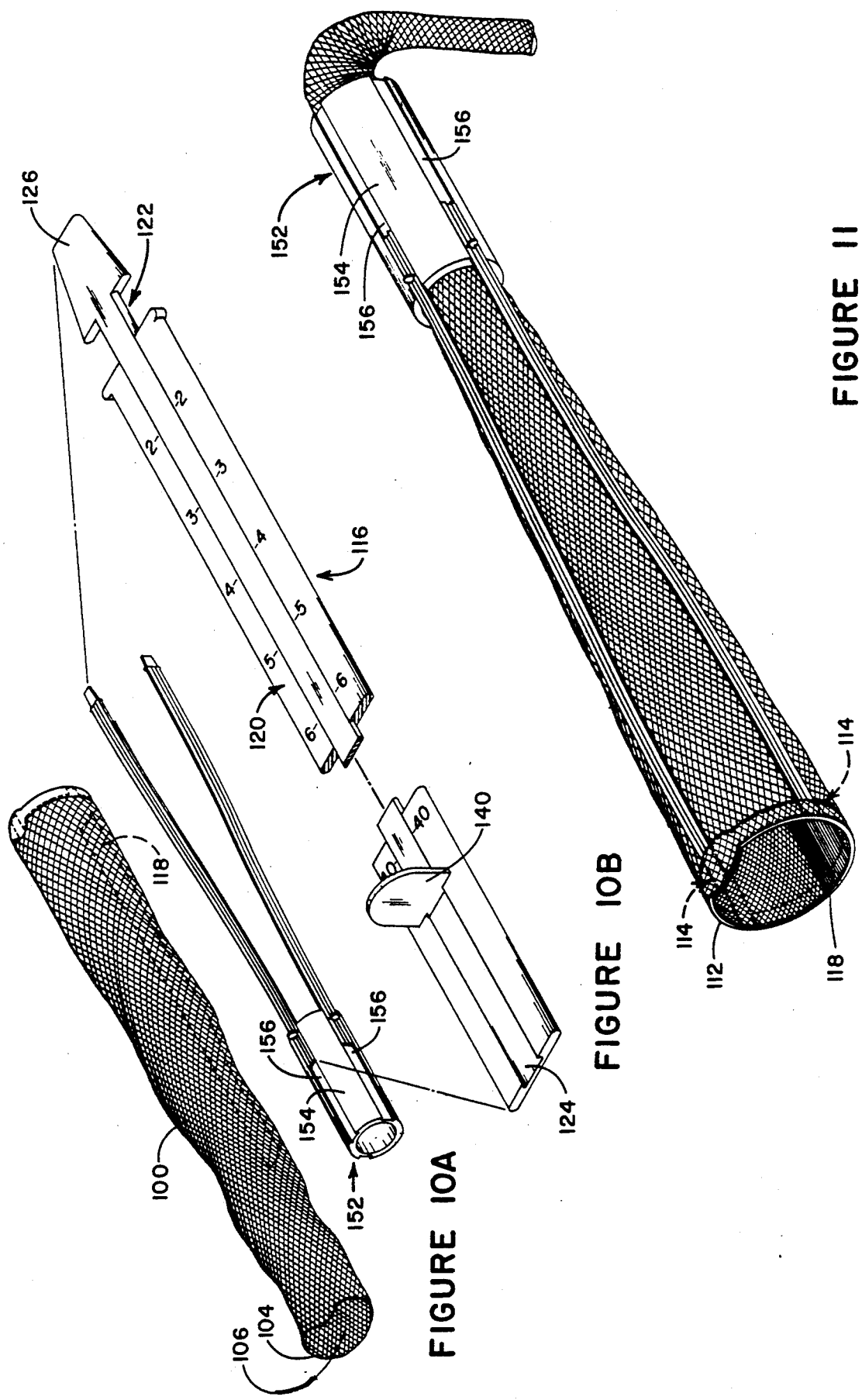

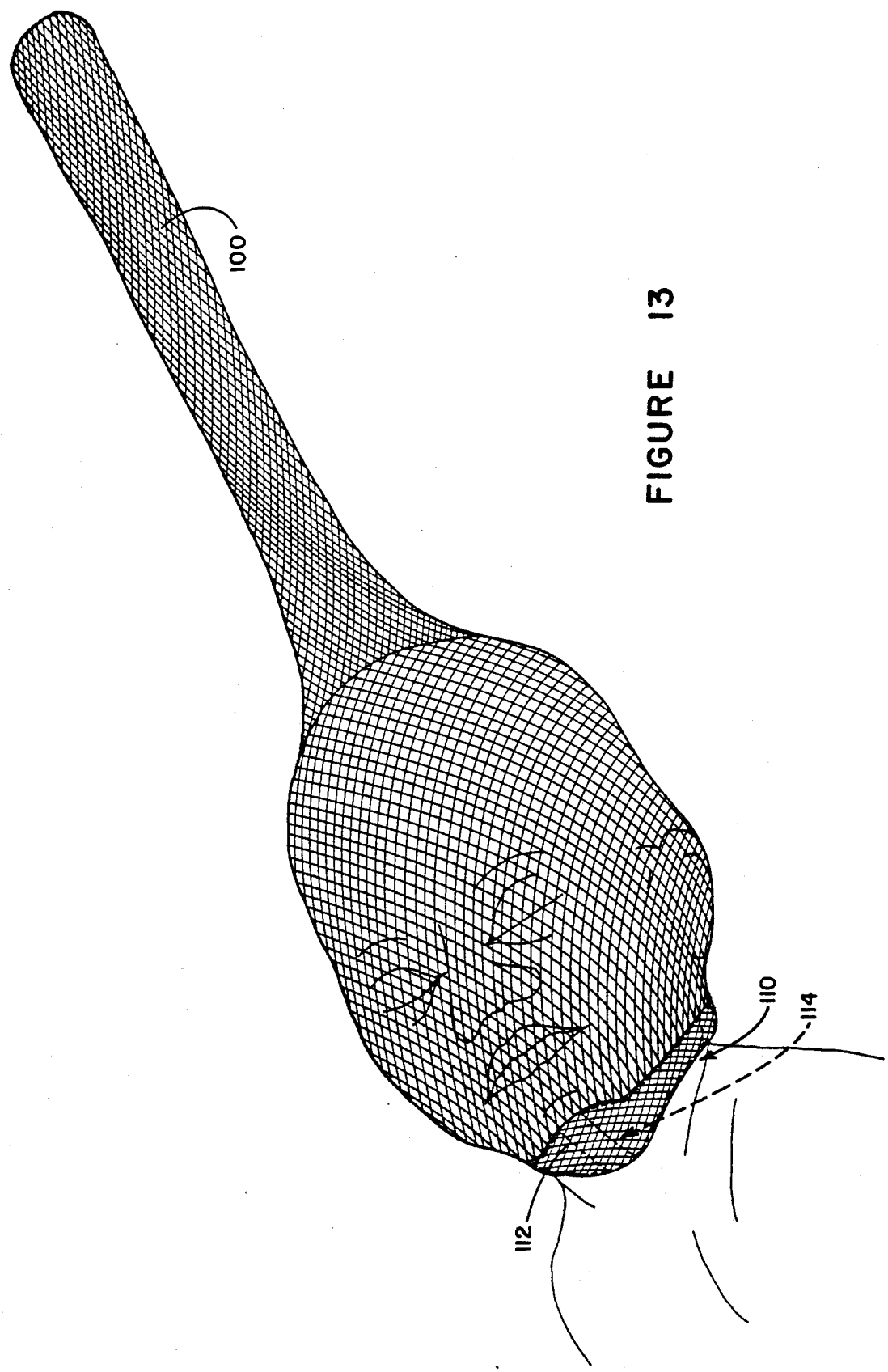

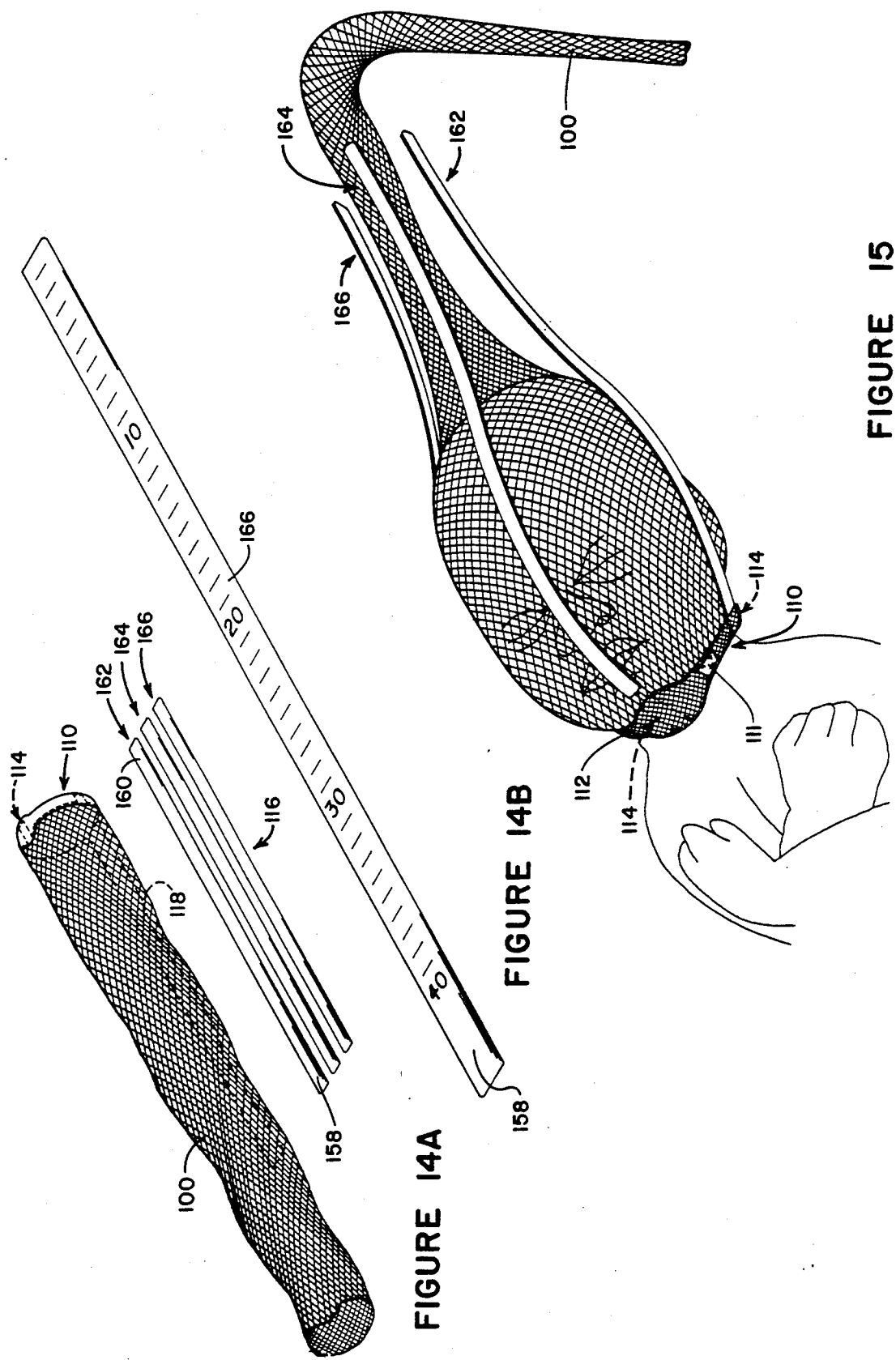

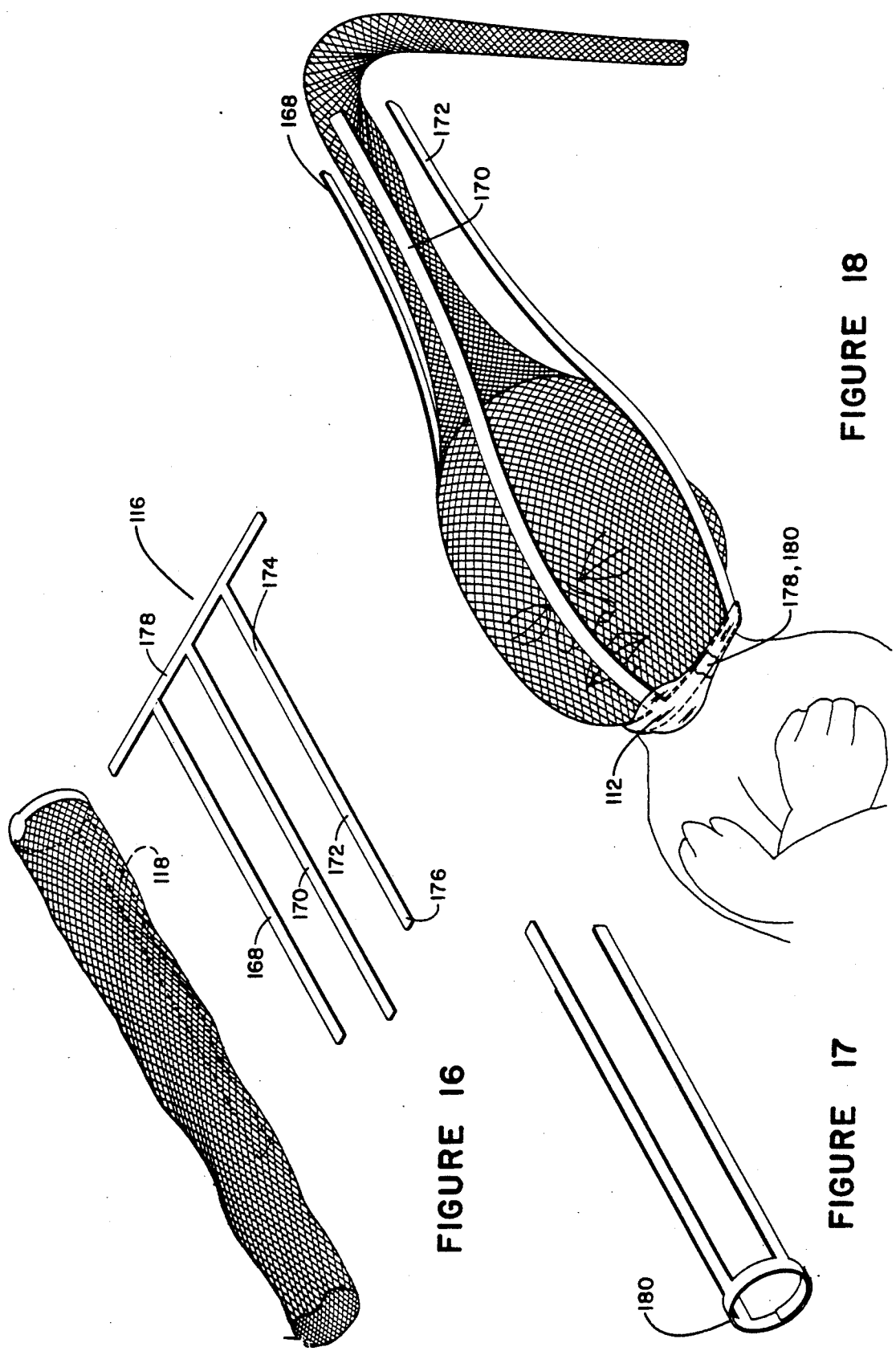

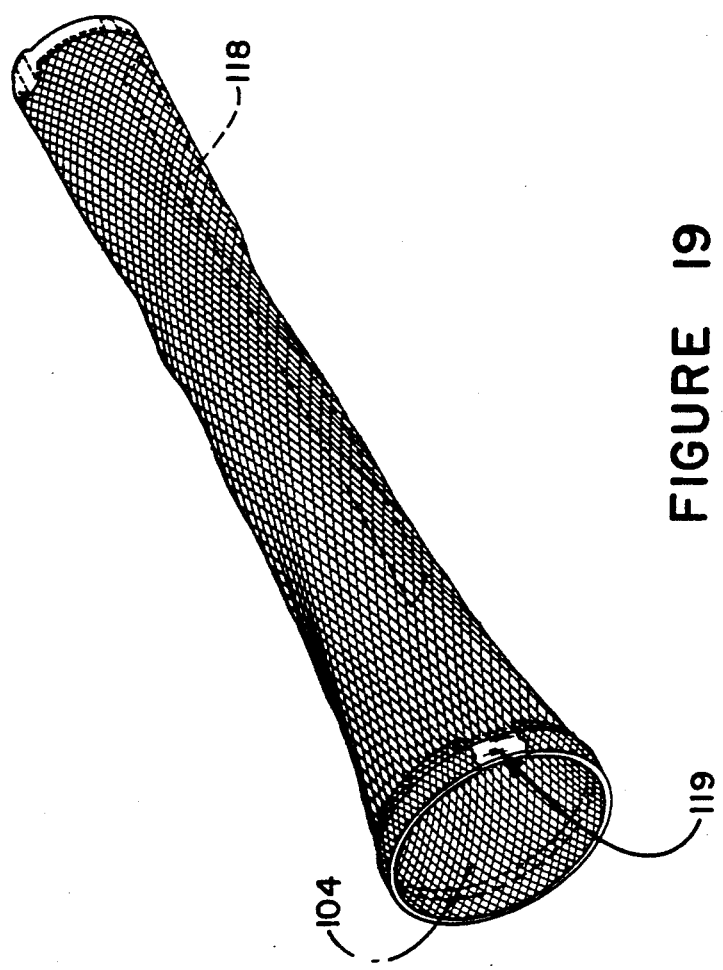

ND SUMMARY OF THE INVENTION

DEVICE FOR ASSISTING CHILDBIRTH

This is a continuation of copending application(s) Ser. No. 07/851,068 filed on Mar. 13, 1992, now abandoned, which is a continuation in part of copending application Ser. No. 07/522,592 filed on May 14, 1990, U.S. Pat. No. 5,122,148.

BACKGROUND OF THE INVENTION

1. Field of the Invention

This invention relates in general to obstetric devices, and more particular to devices useful in removing the baby during vaginal delivery.

2. Prior Art

Today's state of the art obstetrics utilizes various procedures to assist in instances of difficult vaginal deliveries. These procedures basically fall into three categories: version, Caesarian and forceps assisted delivery. In the case of severe cephalo-pelvic disproportion, placenta previa, vaso previa, and other contraindications to vaginal delivery, the "C-Section", whether classic or low transverse, remains the mainstay procedure. However, it has long been recognized that to the extent that C-Section deliveries can be successfully avoided, statistical maternal and fetal benefits will be realized. Even the non-difficult vaginal delivery can benefit from non-traumatic assists.

Many problems may develop during delivery which require assistance from the attending obstetrician to successfully remove the baby from the birth canal. One such problem results from the presenting part of the baby, usually its head, descending too slowly. This is particularly true in the case of the primigravida mother. Even with a completely dilated and effaced cervix, and an adequate pelvis, a fetus might refuse to descend beyond station "+1", especially when the mother is suffering from contraction exhaustion. This can remain a problem even with an assist from administration of oxytocin (Pitocin). This problem is frequently exacerbated by anesthesia, particularly in the instance of epidural anesthesia which frequently produces induced non-beneficial partial atony of the engaged and dedicated muscles. Such partial atony frequently results in non-beneficial, and sometimes hazardous, prolongation of labor. Station "+1" is considered midpelvis and in the usual case is considered too high for a forceps assisted delivery. The risks to the fetus with forceps application at this level are extreme. Forceps cannot be safely used until the presenting part is at least at station "+2", and preferably between stations "+2" and "+3", which is the floor of the perineum.

Modern obstetrics has not developed an alternative to the use of forceps when an assisted natural delivery is indicated, such as when the fetus is consistently exhibiting late decelerations of heartbeat following contractions or is exhibiting nonvariability of the baseline heartbeat rate. Obstetrical forceps are typically, in their various types two bladed affairs which are blindly inserted one blade at a time in a hopefully temporal-cheek position and then articulated together before assisting traction is applied. Actual traction is exerted slightly below or underneath the mandibles. The traction is point concentrated and slippage of the forceps is increased because of natural lubrication, refusal of the fetal skull to conform to existing forceps design, and other known myriad of variables that vary from one fetus-to-pelvis physical relationship to another.

Even proper positioning of the forceps can result in harm to the fetus. For example, in instances of minimal cephalo-pelvic disproportion, the insertion of one blade of the forceps can exacerbate any slight deficiency in birth canal adequacy. In addition the softness, or pliability, of the fetal skull, coupled with the existence of sutures which separate the plates of the skull, render the skull susceptible to trauma associated with metal forceps assisted deliveries.

The problems associated with forceps assisted deliveries are well known, and many attempts have been made to improve forceps design. Examples of the current state of the art in forceps design can be seen in the following patents: U.S. Pat. No. 3,550,595 entitled "Obstetrical Forceps" and issued on Dec. 29, 1970 to Leonard E. Laufe; U.S. Pat. No. 3,605,748 entitled "Obstetrical Forceps" and issued on Sep. 20, 1971 to Hector Salinas-Benavides; U.S. Pat. No. 3,665,925 entitled "Obstetrical Forceps" and issued on May 30, 1972 to Hamo M. Dersookian; U.S. Pat. No. 3,785,381 entitled "Pressure Sensing Obstetrical Forceps" and issued on Jan. 15, 1974 to Brenton R. Lower et al; U.S. Pat. No. 3,789,849 entitled "Obstetrical Forceps" and issued on Feb. 5, 1974 to Leonard E. Laufe et al; and U.S. Pat. No. 3,794,044 entitled "Delivery Forceps" and issued on Feb. 26, 1974 to William O. Vennard.

Despite the long felt need and the large amount of time and effort spent to develop an alternative to forceps, the only assisting device developed which has seen some application is a vacuum extractor. Because of the difficulty in the safe use of this device, it has not proven to be successful and its use has in large measure been abandoned.

OBJECTS AND SUMMARY OF THE INVENTION

It is therefore an object of this invention to provide an assisting device for childbirth which can safely perform substantially all of the functions of forceps.

Another object of this invention is to provide an assisting device for childbirth that is easy to use and reduces the risk of injury to the fetus during childbirth.

Still another object of this invention is to provide an assisting device for childbirth that can be quickly applied to the skull of the fetus by the attending obstetrician.

Still other objects and advantages of this invention shall become apparent from the ensuing descriptions of the invention.

Accordingly,

BRIEF DESCRIPTION OF THE DRAWINGS

FIG. 8 is a three dimensional view of the unborn infant to which the embodiment, as seen in FIG. 7, has been attached.

FIG. 9 is a cut-away view of an unborn infant positioned for vaginal delivery utilizing another embodiment of the invention.

FIG. 10A is a three dimensional view of the handle means of one embodiment of the invention.

FIG. 10b is an enlarged view of the insertion means which can be utilized with the aforementioned handle means.

FIG. 11 is another three dimensional view of one embodiment of the present invention utilizing the handle means.

FIG. 13 is a three dimensional view of the preferred embodiment of the present invention attached to the head of the infant.

FIG. 14A depicts the preferred embodiment of a plurality of the insertion means.

FIG. 14B is an enlarged view of one of the insertion means as seen in 14A.

FIG. 15 is a three dimensional view of the preferred embodiment of the invention.

FIG. 16 depicts an alternate embodiment of the present invention.

FIG. 17 is another view of the embodiment seen in FIG. 16.

FIG. 18 is a three dimensional view of the embodiment seen in FIG. 177 attached to the head of the infant.

FIG. 19 is a three dimensional view of another embodiment of the invention.

PREFERRED EMBODIMENTS OF THE INVENTION

Figure 1:
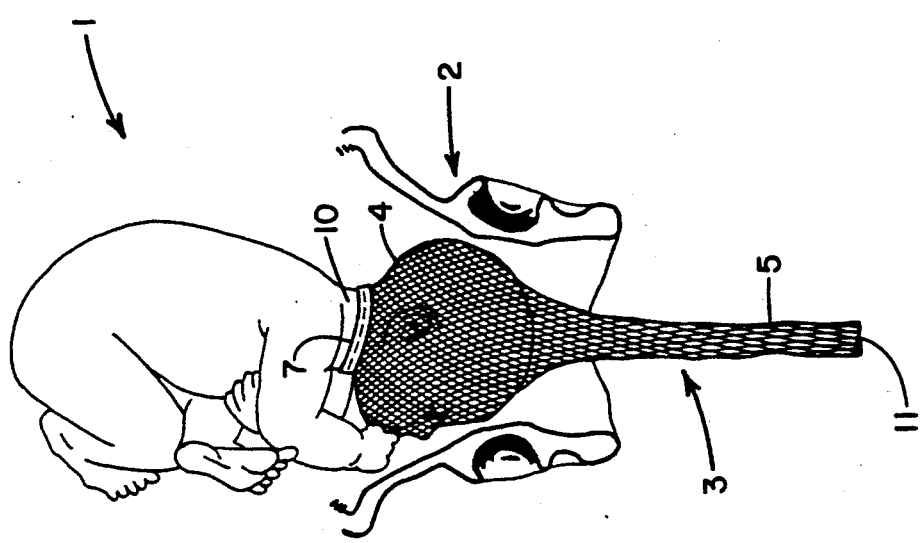
FIG. 1 is cutaway view of an unborn infant positioned for vaginal delivery to which has been attached an embodiment of this invention.

Referring now to FIG. 1 which depicts one embodiment of the present invention, a fetus, generally denoted by numeral 1, is depicted positioned in a cutaway of a portion of a woman's birth canal 2 having the childbirth assist device 3 attached to its head 4 and trailing outside of the vagina area of the birth canal 2.

Figure 2:
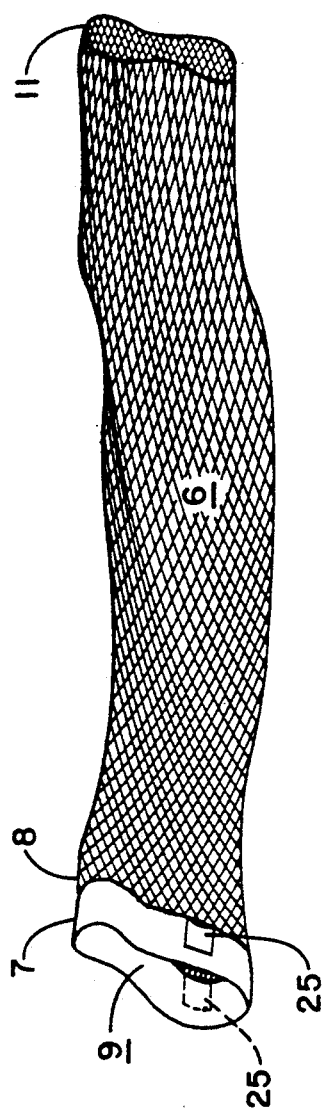
FIG. 2 is a three dimensional view of one embodiment of this invention.

In its broadest context as shown in FIG. 2, the device 3 comprises an elongated sock-like member 5 open at both ends not only to allow a physician to fit his hand and arm in passageway 6 of member 5 for rotational purposes, but also to allow the head 4 to fit into passageway 6. In addition device 3 comprises a collar 7 attached at one end 8 of member 5 which can be adjusted to restrict the size of opening 9 formed at end 8.

In one embodiment, member 5 is constructed from material having some elasticity characteristics, and more preferably from a material selected from a group consisting of natural fibers or man-made plastic fibers. Natural fibers could include cotton, linen and silk. Plastic fibers could include nylon, dacron and rayon. Preferably the degree of elasticity should be at least to a degree such that the material would begin to stretch before the pulling force exceeded a predetermined amount. That amount would depend on the stage of development of the fetus, as well as other known factors. The degree of elasticity is preferably set so the pulling force is less than that which would harm the fetus. Member 5 is also preferably pliable so that it can be shaped and easily moved in position about head 4. In another preferred embodiment the material will be constructed from a mesh material, the size of the mesh would preferably be sufficiently small enough to reduce chances of non-beneficial oral ingestion of toxic meconium by the fetus. In still another preferred embodiment the fabrics would be sterilized and lubricated with K-Y jelly to reduce or prevent the fabric from absorbing the natural lubricants within the womb. K-Y jelly is a brand name for a product sold by Johnson & Johnson.

Figure 4:
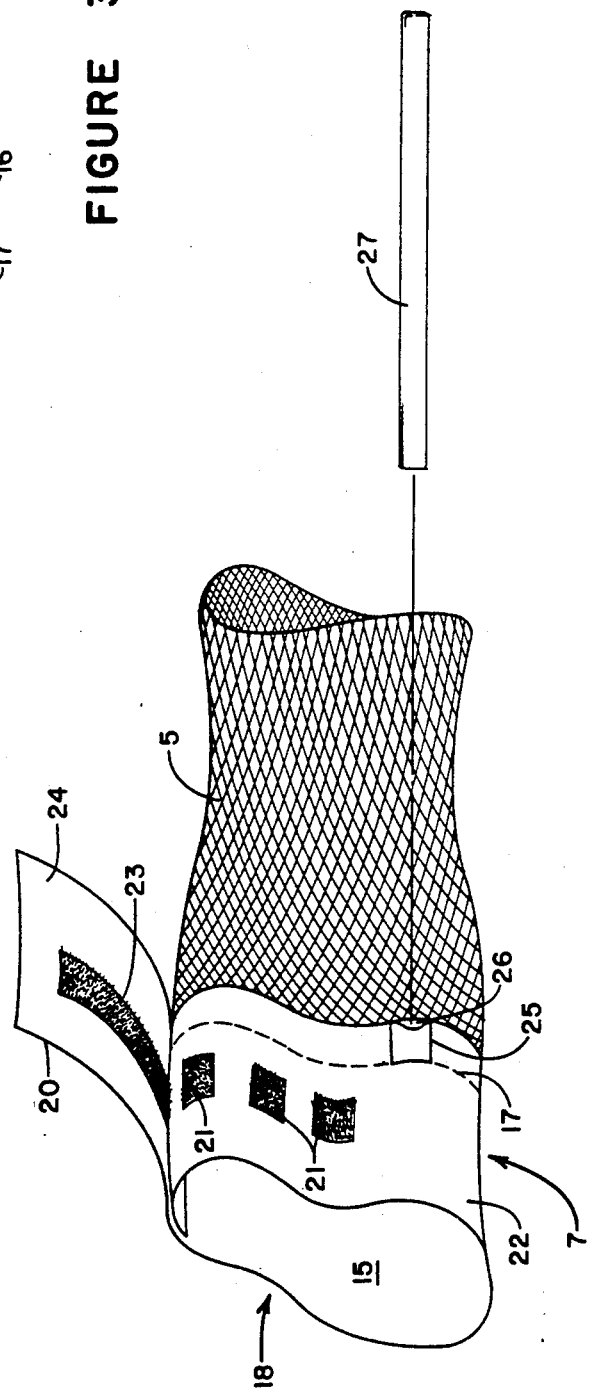
FIG. 4 is an enlarged view of another embodiment of the closure means forming part of this invention.

The member 5, which in the preferred embodiment will be constructed of the aforementioned mesh material, will comprise an angular mesh as seen at 5a of FIG. 4. Once the member 5 has been placed in position over the head of the infant, this angular mesh will impart a uniform distribution of forces, as in the manner of the Chinese handcuff, as the member 5 is pulled in a linear direction, with respect to the passageway 6. In other words, all areas of the infants head which are in contact with the mesh of member 5 will have exerted against it a gripping axial force created by the diminishment of size of the angular mesh secondary to traction; thus, as the member 5 is pulled, all of the pulling force will be distributed across the area which is in contact with the infant's head and axial gripping of the child's head has been initiated. Also, in the preferred embodiment, the angular mesh is constructed of a synthetic or natural fiber. The fiber can be round or elliptical in cross-section and be mono-filament or bi-filament fibers.

In the embodiment shown in FIG. 2, collar 7 is constructed of an elastic material which can be stretched to fit about head 4 and then will contract to an extent to fit loosely about the neck area 10 of the fetus 1. In this manner collar 7 will not choke the fetus 1, but also will not easily slip over the head 4 when the physician pulls on end 11 of member 5 during the delivery process as described below.

Figure 3:
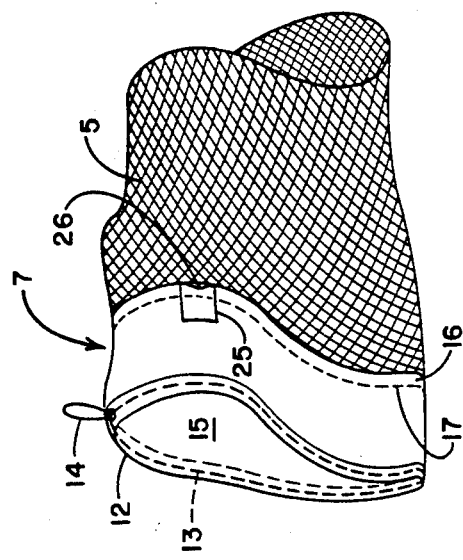
FIG. 3 is an enlarged view of one embodiment of the closure means forming part of this invention.

In another embodiment as shown in FIG. 3, collar 7 is constructed from a pliable material wherein one edge section 12 has been folded over and stitched to itself to form a drawstring pocket 13 in which drawstring 14 has been placed. When drawstring 14 is pulled opening 15 is restricted. The other edge section 16 of collar 7 is stitched or otherwise connected to member 5 along line 17.

In a third embodiment as shown in FIG. 4, collar 7 is constructed of a strip 18 of pliable material having one section 19 stitched or otherwise connected substantially about the perimeter of end 8, and having another section 20 that can extend over a portion of the first section 19. Strips 21 of Velcro or similar material are attached to side 22 of section 19 in a position to be alignable with at least a portion of the strips 23 of Velcro or similar material attached to side 24 of section 20. Velcro is a registered trademark of VELCRO INDUSTRIES, B.V. (NETHERLANDS CORPORATION) identifying hook and loop fastener systems. The size of opening 15 can be adjusted by changing the alignment of the strips 21 and 23. Opening size is then maintained by contacting the overlapping sections of the strips to one another.

In the embodiment as illustrated in FIGS. 2–4, collar 7 is provided with one or more pockets, preferably two or more, formed by a piece 25 of fabric that is attached on three sides to collar 7 to form an opening 26 facing toward member 5. The opening 2 will be large enough so that one end of wand 27 can be inserted through the opening. Wand 27 is preferably constructed from a flexible material, such as plastic, that would will allow it to conform to the shape of the fetus' head, yet rigid enough to allow it to be used to push collar 7 around the fetus' head when positioning device 3.

Figures 5, 6A, 6B, 7:
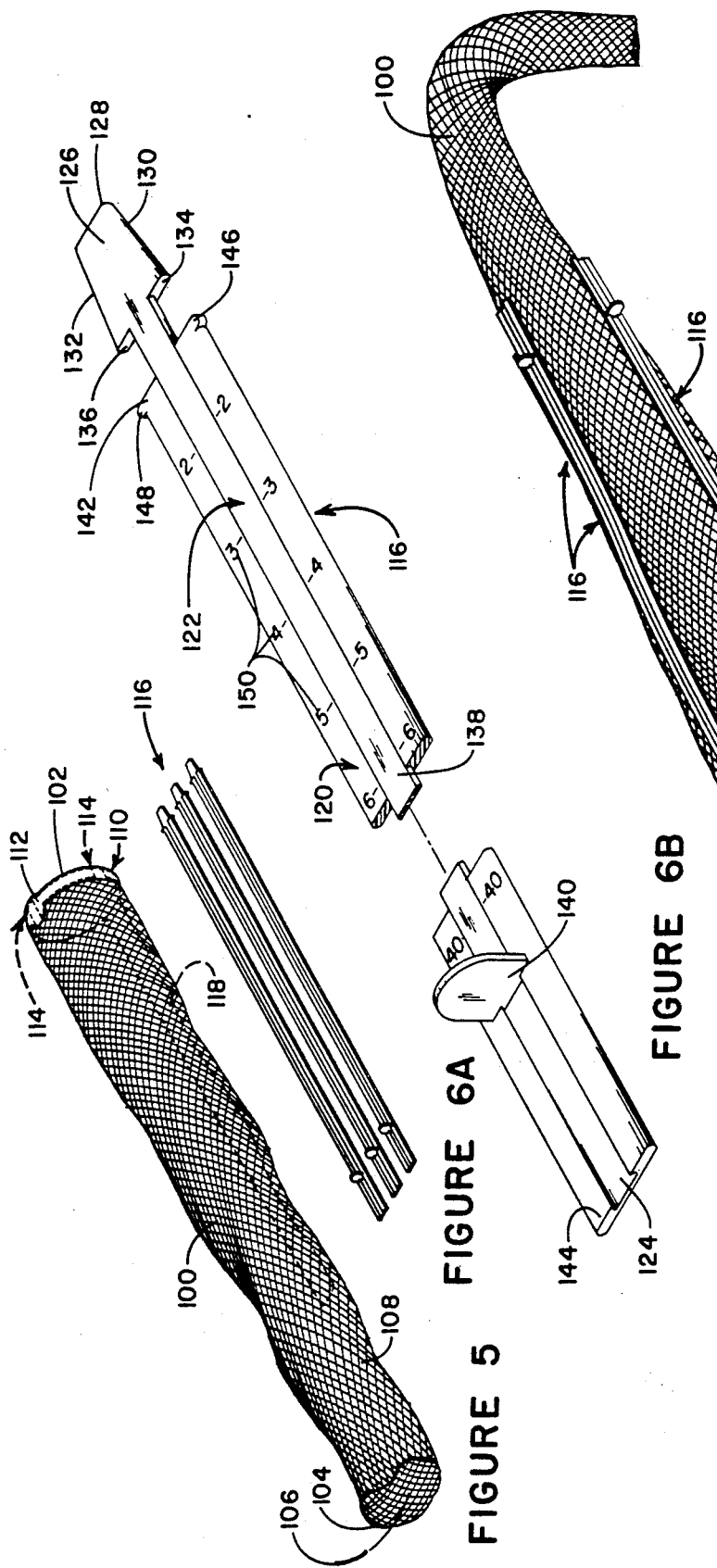
FIG. 5 is a three dimensional view of another embodiment of this invention.
FIG. 6A is a three dimensional view of one embodiment of the insertion means.
FIG. 6B is an enlarged view of the insertion means seen in FIG. 6A.
FIG. 7 is a three dimensional view of one embodiment of this invention which utilizes the insertion means of FIGS. 6A and 6B.

Referring to FIG. 5, another embodiment of the present invention is depicted. The elongated member 100 has a first end 102 and a second end 104, with a passageway 106 defined therein. The member is constructed of the angular mesh material 108, as previously described. The collar means is constructed of pliable material and is similar in design to the collar 7 in that collar 110 is connected to the first end 102 of the elongated member 100, so that the first end 102 encircles the infant's neck. The collar means 110 will have an elastic band 111, as seen in FIG. 8, sewn into the hem of the collar and sized to rest at a diameter sufficient to preclude carotid or larynx compression and to expand to a diameter sufficient to permit application over the largest portion of the fetal skull.

The collar means 110 will also contain a widened below chin segment 112, which is also illustrated in FIG. 7. The chin segment 112 is generally a protuberance on the collar means 110 which is adapted so that the infants chin can be abutted adjacent thereto when the member 100 is being pulled during childbirth. The collar means 110 will also comprise pocket means 114, similar to the aforementioned pockets 25, for receiving the wand or wands 116, which is also referred to as the insertion means 116, as seen in FIG. 6A.

The elongated member 100 can also posteriorly contain a linear mesh segment 118 which is attached to the first end 102 and is best see in FIG. 7. The linear mesh segment 114 will exhibit enhanced tensile properties so that during delivery, the fetus' skull may be tilted in a vertical plane relative to the sternum by applying traction to the linear mesh segment 114 to achieve increased flexion.

As seen in FIG. 19, the second end 104 can contain an access ring means 119, which is a rigid, plastic ring of an internal diameter equal to or slightly larger than the internal diameter of passageway 106. The access means will permit the immediate access through the cylinder to the fetal skull for usual and necessary obstetrical procedures.

Referring to FIGS. 6A and 6B, one embodiment of the insert means will now be described. The insertion means 116, or wand 27 as referred to earlier in this application, is provided for inserting the collar means 110 over the infants head. The insertion means, as seen in FIGS. 6A and 6B, will have a first and second member 120, and 122. The second member 122 will overlay the first member 120 in the slotted groove 124 of member 120.

Member 120 will have a first end wedge section 126, with said wedge section having a first surface 128 which extends to angled shoulders 130 and 132. Shoulder 130 terminates at the back surface 134 and shoulder 132 terminates at the back surface 136. Both surfaces 134 and 136 extend to the elongated segment 138, with the elongated segment extending to the perpendicular segment 140, also known as the thumb tab.

The elongated segment 138 is slidably disposed within the groove 124 of the first member 120 so that the segment may be moved outward or inward in a telescopic fashion. Thus, if the operator is holding first member 120, and exerts a force on the thumb tab 140, the second member will be moved away relative to the first member 120.

First member 120 will have a first and second end 142,144, with the first end containing ridges 146 and 148. Ridges 146 and 148 will be sized so that as the ridges are placed within the pockets 112, the ridges 146 and 148 engage the pocket with some mechanical restriction. First member will also have defined thereon graduations 150, marked in centimeters.

Referring now to FIG. 7, the insertion means 116 have been inserted into the pocket means 114 before the apparatus is attached to the fetus. In this position, the ridges 148 and 146 are fitted into pocket 112 with some mechanical restriction so that the ridges do not easily slip out of the pockets during positioning of the apparatus. In FIG. 8, the invention is attached to the infant's head. Hence, utilizing the insertion means 116, it can be seen that the collar means 110 has been positioned around the infants neck and the chin segment 112 has been placed beneath the mandible area. The elastic 111 of the collar means 110 will, therefore, cause the collar to surround the neck so that the elongated member 100 does not slip off.

After the proper position has been obtained about the fetus, the insertion means 116 can be removed from the pockets 114 as seen in FIG. 8. This will entail the physician having to hold member 120, then begin pushing second member 122 by pushing on the thumb tab 140 in a direction such that surface 128 is constrained against the pocket means 114. This will cause the wedge member 126 to continue to act against the pocket member 112 and thereby cause the collar means to move, but because the member 120 is being held stationary, the ridges 146 and 148 will be slipped out of the pocket 112. Conversely, the physician can hold the thumb tab 140 stationary, and pull on the first member 120 thereby disengaging the ridges 146 and 148 from the pockets.

FIG. 9 shows a cut-away view of the infant in the birth canal after placement of the collar means 110 in the position for removal of the infant. As can be seen from this view, the chin segment 112 is centered below the mandibles. As noted earlier, as the elongated member 100 is pulled by the operator of the device, which in most cases is a medical doctor, the axial gripping forces of the mesh will distribute the pulling forces to all areas of the mesh which have been expanded by the infant's head.

Referring to FIGS. 10A and B, handle means 152 is shown which may be used for holding and placing the aforementioned insertion means 116 into the pocket means 114. The handle means comprises generally of a tubular cylinder 154 which has an internal diameter roughly the size of the passageway 106. The cylinder 154 will contain a plurality of slots 156 which will have fitted therein the first member 120 of the insertion means 116. In particular, second end 122 will be inserted into one of the slots 156. In the preferred embodiment of the handle means 152, there will be three slots, such that three wands 116 can be attached to the handle means 152.

As seen in FIG. 11, the handle means 152 has been attached to the elongated member 100 by placing the second end 144 of wands 116 into the slots 156, and by having the wedge section 126 of the second member 122 engaged with the pocket means 114. As seen in FIG. 11, the apparatus, which includes the handle means 152 containing the insertion means 116 is now available for placement over the fetal head.

Figure 12:
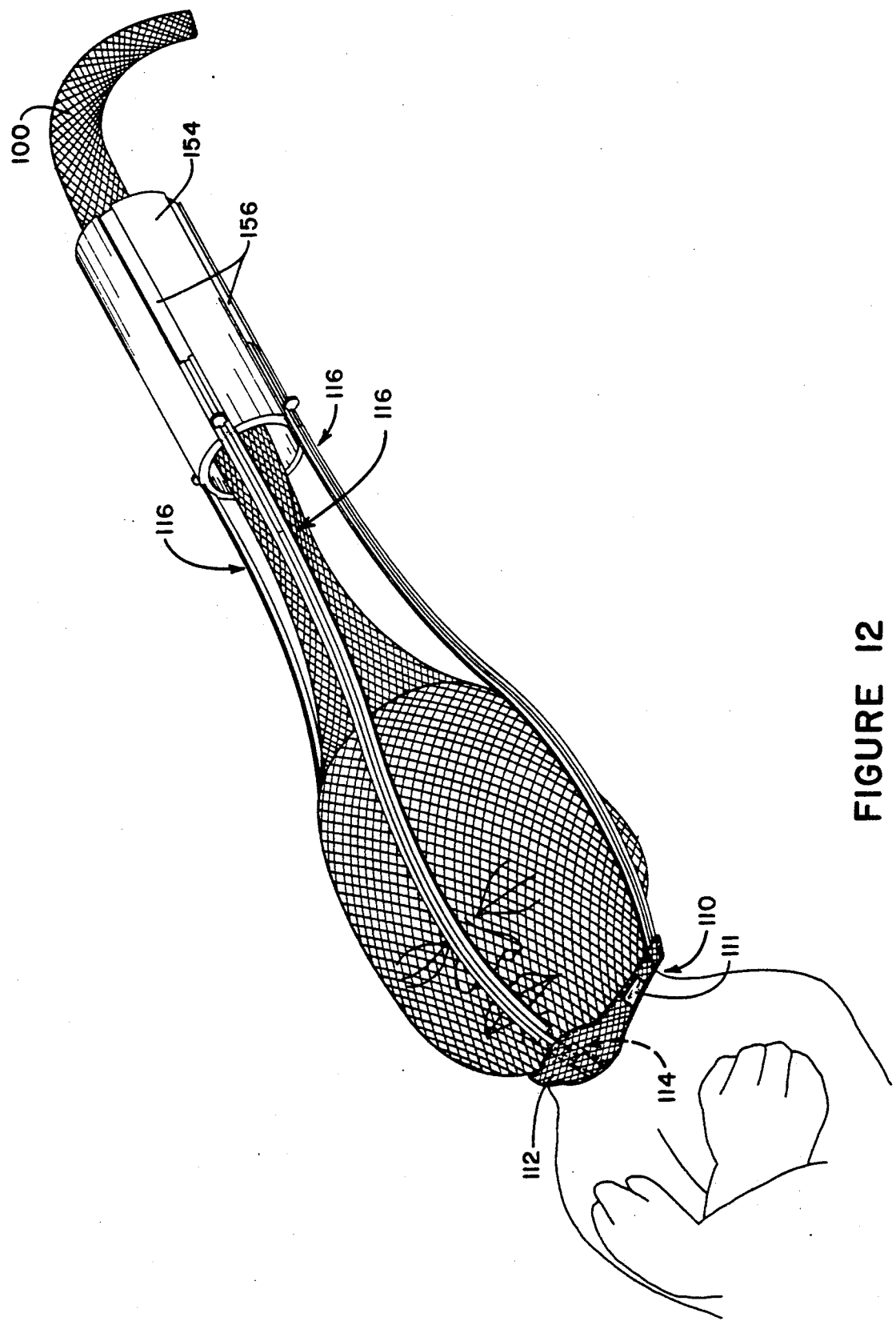
FIG. 12 is a three dimensional view of the handle means being utilized to position one embodiment of the present invention over the head of the infant.

In order to remove the handle means 152, disengagement of wands 116 with the pocket means is accomplished as previously discussed. FIG. 12 shows the position of the handle means 152 after the apparatus has been placed over the head of the fetus and removal of the insertion means has begun. FIG. 12 also shows the elastic band 111 of the collar means 110.

Turning to FIG. 13, the elongated member 100, along the collar means 110 and chin segment 112, is shown after the insertion means 116 have been removed. As can be seen, the angular mesh has been expanded by the head of the infant so that the previously described axial gripping force will be applied once the doctor has exerted a lateral pull on member 100 to assist in the removal of the infant from the birth canal.

Referring now to FIGS. 14 and 15, the preferred embodiments of the present invention will be discussed. The insertion means 116 consist of a single, flat, one-piece flexible wand with a first end 158 and second end 160. In the preferred embodiment, three flexible wands will be employed, 162, 164 and 166. The single wands, 162, 164 and 166, will have already been placed within the pockets 114 which are disposed about the collar means 110 before the apparatus is placed over the fetal head.

FIG. 14B shows an enlarged view of the wand 166, with graduations in centimeters. The first end 158 will fit with some mechanical constriction into the pocket means 114, as can also be seen in FIG. 15. Thus, as shown in FIG. 15, the wands 162, 164, and 166 are positioned within the pockets 114 of collar 110. The first end 158 of wand 164 is illustrated as being pulled away from the collar means 110. In other words, the wand 164 has been pushed downward into the proper below mandible position by manipulating the wand downward. Next, wands 162 and 166 are manipulated, and once the proper position is reached, the wands 162, 164, and 166 can be removed by pulling the wands away from the pockets, which is shown by the relative position of wand 164 to the collar means 110.

FIG. 16 depicts another embodiment of the insertion means 116. In this embodiment, three elongated, flat, elongated wands 168, 170 and 172. Each of these wands will have a first end 174 and a second end 176, with the first end 174 of the wands 168, 170 and 172 being joined to a perpendicular member 178 which forms a collar 180, as seen in FIG. 17. In this embodiment, the perpendicular member 178 will be fitted into a folded latex hem of the woven mesh cylinder. The internal diameter of collar 180 at rest will be sufficient to preclude compression of the carotids or of the larynx and with an expansion diameter sufficient to permit application over the fetal skull. FIG. 18 shows the member 178 in place, as the member 178 has been folded to form a collar 180.

In operation, the device 3, as shown in the embodiments of FIGS. 1-4, is first positioned on the top of the fetus, head 4 with the wands 27 fitted into pockets 25. The wands 27 are then maneuvered by pushing the ends of each wand 27 against the inside walls of their respective pocket 25 until the device is slipped over the fetus' head. When the collar 7 extends posterior to the head 4 the physician then adjusts collar 7 so that it fits loosely about neck area 10, but is restricted so as not to easily slip over the head 4. The physician then grabs the end 11 and applies a pulling force which will cause the collar 7 to exert an equalized and evenly distributed resistance to the pulling force sufficient to initiate axial uniform gripping of the fetal skull in the manner of the Chinese Handcuff. This pulling force will assist the mother in the natural childbirth or in positioning the fetus 1 closer to position "+2" and "+3" where if needed forceps can be used more safely. Once the fetus has been removed, the physician then removes device 3 from the head 4. The device is then preferably discarded and not reused. In many cases device 3 may eliminate the need to use forceps during the delivery.

As regards the method of assisting the delivery of an infant during childbirth utilizing the elongated member of FIG. 5 and the insertion means of FIGS. 14A and B, first, the insertion means, which comprises of members 162, 164, and 166, are fitted into the pocket means 114. Then, the collar means 110 is guided over the infants head by applying force to the insertion means until the collar is anteriorly below chin depth and posteriorly below the smallest portion of fetal skull as shown in FIG. 13.

Next, the device is pulled from the second end 104 of the elongated member 100, and the pulling force exerted on the second end 104 will be uniformly distributed about the fetus' skull due to the axial gripping of the mesh. Continuous or intermittent pulling, as needed, on the second end 104 will result in assistance in delivery of the infant.

The delivery of the child may also be accomplished with a the other embodiments heretofore disclosed. For instance, the insertion means 116 may be employed, instead of use of the members 162, 164, and 166, for guiding the collar means 110 over the infants head. In such a case, after the apparatus has been positioned through manipulation of the first and second members, 120 and 122, the insertion means 116 will be withdrawn as heretofore described. Also, the handle means 152 may also be employed, as previously described. Finally, the invention should be understood to assist in the delivery of any type of fetus, and not limited to human fetus'. In other words, the embodiments disclosed would also be applicable to veterinary obstetrics in deliveries of such mammals as horses, cattle, and sheep.

There are of course other alternate embodiments which are obvious from the foregoing descriptions of the invention which are intended to be included within the scope of the invention as defined by the following claims.

I claim:

1. An apparatus for assisting delivery of a fetus, comprising:
 an elongated member having a tubular passageway formed therethrough, said member having a first end and a second end;
 collar means, connected to the first end of said elongated member, for encircling the neck of the fetus so that the first end of said elongated member surrounds the fetus' head;
 insertion means for inserting said collar means over the fetal head and wherein said insertion means includes at least one elongated member which is capable of transmitting a force;
 wherein said collar means further contains pocket means for receiving said insertion means and transmitting the force of said insertion means to said collar such that said insertion member moves said collar means relative to the fetus, and elastic means for providing a minimum inner diameter capable of expanding to a diameter sufficient to permit application over the largest portion of the head of said fetus; wherein said elongated member of said insertion means comprises:
 a first member; and a second member overlaying said first member and cooperating with said first member so that said second member can be extended relative to said first member.

2. The apparatus of claim 1, wherein said first member contains graduation means for determining the relative movement of said first member relative to said second member; and said second member comprises a first end and a second end, wherein said first end has a tapered surface and said second end has a projection formed thereon.

3. The apparatus of claim 2, wherein said first and second member is constructed of plastic.

4. An apparatus for assisting delivery of a fetus, comprising:

an elongated member having a tubular passageway formed therethrough, said member having a first end and a second end;

collar means, connected to the first end of said elongated member, for encircling the neck of the fetus so that the first end of said elongated member surrounds the fetus' head;

insertion means for inserting said collar means over the fetal head and wherein said insertion means includes at least one elongated member which is capable of transmitting a force, and wherein said insertion means includes a plurality of flexible wands, each of said wands having a first end and a second end, and wherein said wands comprise a first member, and a second member overlaying said first member and cooperating with said first member so that said second member can be extended relative to said first member;

and wherein said collar means further contains pocket means for receiving said insertion means and transmitting the force of said insertion means to said collar such that said insertion member moves said collar means relative to the fetus, and elastic means for providing a minimum inner diameter capable of expanding to a diameter sufficient to permit application over the largest portion of the head of said fetus.

5. The apparatus of claim 4, further comprising:

handle means for holding said wands at the first end of said wands, and wherein said handle means includes a tubular structure with a plurality of slots to receive said first ends of said wands.

6. A method of assisting the delivery of an infant during birth, the method comprising the steps of:

a) positioning an apparatus over the fetal skull, said apparatus including: an elongated mesh member having a first and second end; collar means, connected to the first end of said elongated member, for encircling the fetal neck so that the first end of said elongated member surrounds the infant's head and wherein said collar means contains an opening; and, at least one insertion member placed within said opening, and wherein said insertion member includes a first and second portion having a first end and a second end, the second end having a shoulder engaged in said opening, and wherein said first and second portions are overlaid so that said first and second portions may be telescoped relative to each other;

b) guiding said collar means over the fetal head by applying force to said insertion member until said collar means is posterior to the infant's head;

c) adjusting said collar means so that said collar means fits loosely about the fetal neck, but is restricted so as not to easily slip over the fetal head and further includes the steps of:

manipulating said insertion means until the correct position is obtained, and removing said insertion member by pushing on the first portion of said insertion member while holding onto the second portion so that the shoulder becomes disengaged with said opening, and withdrawing the first portion and second portion from said apparatus;

d) pulling said device at said second end so that said collar means exerts an equalized and evenly distributed resistance to pulling sufficient to initiate axial gripping by said mesh of said elongated member about the fetal head; and e) delivering the child by vaginal birth.

7. A device for assisting the delivery of an infant during childbirth comprising:

a cylindrical member having a tubular passageway formed therethrough, said member having a first end and a second end;

an elongated insertion member having a first end and a second end;

a collar connected to the first end of said cylindrical member and wherein said collar includes an elastic band, and at least one opening formed in said collar for receiving the insertion member;

linear reinforcing means, connected to the first end of said cylindrical member, for reinforcing said cylindrical member so that said linear reinforcing means exhibits enhanced tensile properties;

and wherein said cylindrical member and linear reinforcing means are constructed of a pliable material.

8. The device of claim 7 wherein said material is a natural fiber.

9. The device of claim 7 wherein said material is a synthetic fiber.

10. The device of claim 9, wherein said insertion member is a flexible wand having defined thereon graduations so that the relative position of the wand with relation to the cylindrical member can be determined.

11. The device of claim 10 wherein the collar further includes:

a protuberance formed on the collar which is adapted to rest against the chin of the infant.

12. The device of claim 11, wherein said collar contains three openings disposed about said collar for receiving three insertion members.

13. The device of claim 12, wherein the second end of said cylindrical member has connected thereto and access ring for access to the passageway.

* * * * *